United States Patent [19]

Lennox

[11] Patent Number: 4,966,593
[45] Date of Patent: Oct. 30, 1990

[54] DISPOSABLE HYPODERMIC SYRINGE WITH RETRACTABLE NEEDLE

[75] Inventor: James J. Lennox, Berwick, Pa.

[73] Assignee: Design Specialties Laboratories, Kingston, Pa.

[21] Appl. No.: 319,154

[22] Filed: Mar. 6, 1989

[51] Int. Cl.⁵ ............................................. A61M 5/32
[52] U.S. Cl. .................... 604/198; 604/263; 604/110
[58] Field of Search ............... 604/198, 195, 110, 263, 604/187, 218

[56] References Cited

U.S. PATENT DOCUMENTS

| | | |
|---|---|---|
| 2,674,246 | 4/1954 | Bower . |
| 2,876,770 | 3/1959 | White . |
| 3,306,290 | 2/1967 | Weltman . |
| 3,314,428 | 4/1967 | Johnson et al. . |
| 3,890,971 | 6/1975 | Leeson et al. . |
| 4,026,287 | 5/1977 | Haller . |
| 4,425,120 | 1/1984 | Sampson et al. . |
| 4,573,976 | 3/1986 | Sampson et al. . |
| 4,592,744 | 6/1986 | Jagger et al. . |
| 4,631,057 | 12/1986 | Mitchell . |
| 4,643,199 | 2/1987 | Jennings, Jr. et al. . |
| 4,650,468 | 3/1987 | Jennings, Jr. . |
| 4,664,654 | 5/1987 | Strauss . |
| 4,675,005 | 6/1987 | DeLuccia . |
| 4,747,829 | 5/1988 | Jacob et al. . |
| 4,747,831 | 5/1988 | Kulli . |
| 4,767,413 | 8/1988 | Haber et al. . |
| 4,781,684 | 11/1988 | Trenner . |
| 4,813,940 | 3/1989 | Parry ................................ 604/198 |
| 4,838,869 | 6/1989 | Allard ............................... 604/195 |

FOREIGN PATENT DOCUMENTS

89/00435 1/1989 PCT Int'l Appl. ................ 604/110

*Primary Examiner*—John D. Yasko
*Attorney, Agent, or Firm*—Nies, Kurz, Bergert & Tamburro

[57] ABSTRACT

A disposable hypodermic syringe capable of use only one time and including a needle which is automatically retracted within a tubular housing after use to prevent accidental needle sticks. The needle is normally locked in an extended position for normal injection use but then is automatically released through a release mechanism actuated by the same forward movement of the plunger within the syringe as is used to normally dispense the fluid from the syringe.

12 Claims, 2 Drawing Sheets

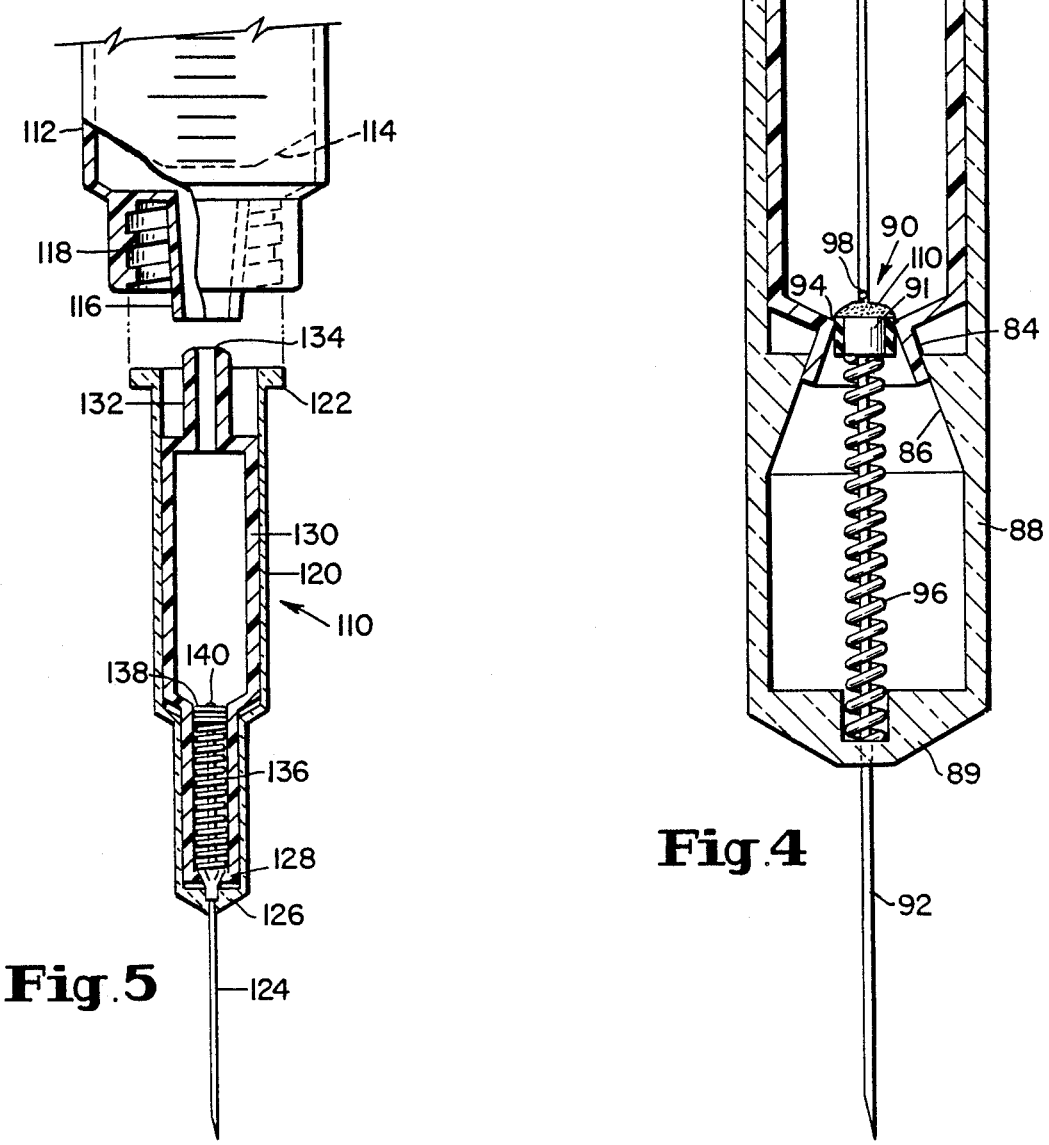

DISPOSABLE HYPODERMIC SYRINGE WITH RETRACTABLE NEEDLE

BACKGROUND OF THE INVENTION

This invention relates generally to disposable hypodermic syringes and more particularly to a novel hypodermic syringe having a needle assembly which is automatically retracted within a tubular housing after the syringe has been used to inject the fluid within a patient.

A growing concern within the health care field is the exposure of health care workers such as doctors and nurses to dangerous diseases such as hepatitis and acquired immuno deficiency syndrome (AIDS) transmitted by way of accidental needle sticks from contaminated used needles.

Accidental needle sticks often occur after use when a worker attempts to recap the used contaminated needle and accidentally sticks himself, or when a used needle is left on a work surface where other workers may accidentally stick themselves. Various proposals have been offered in the past for recapping, shielding or retracting used needles to prevent accidental sticks. Typical proposals are illustrated in prior U.S. Pat. Nos. 3,306,290, 4,026,287, 4,592,744, 4,747,829, 4,747,831, and 4,767,413. While the myriad of proposals exemplified by the designs illustrated in these prior patents serve to accentuate the dangers of exposure to diseases and the concerns of the medical industry none of the prior proposals has totally eliminated the dangers nor has any been widely accepted for use.

Also of concern among health officials is the spread of disease caused by the common practice among drug addicts of reusing or sharing used needles.

SUMMARY OF THE INVENTION

Accordingly the primary object of this invention is to provide a novel hypodermic syringe having a needle assembly which is automatically retracted within a tubular housing after use and which can not be reused again.

Another object of the invention resides in the provision of the above novel syringe wherein the needle is normally locked in an extended position for use and immediately after use is automatically released and retracted within the tubular housing to avoid exposure of medical workers to the used contaminated needle.

Still another object of the invention resides in the provision of the above novel syringe wherein the locking means for the needle is released by an actuator which is engaged by the plunger of the syringe at the end of the stroke so as to immediately and automatically release the needle for retraction within the tubular housing.

Still another object of the invention resides in the provision of the above novel syringe which is operated by one hand, the actuating means being engaged by the plunger and moved forwardly therewith at the end of the plunger's stroke to automatically release the needle for retraction within the tubular housing.

A further object of the invention resides in the provision of the above novel syringe which is easy and convenient to operate with one hand and enables the needle to immediately and automatically be retracted within the protective tubular housing as it is withdrawn from the patient. Consequently the health person experiences no exposure whatever to the used contaminated needle, and the needle can not be reused again.

Still another object of the invention resides in the provision of the above novel syringe wherein the needle once retracted within the tubular housing is retained therein.

These and other objects of the invention will become apparent as the description proceeds in connection with the accompanying drawings.

BRIEF DESCRIPTION OF DRAWINGS

FIG. 3 is an enlarged fragmentary section illustrating the locking mechanism for the extended needle as shown in FIG. 1;

FIG. 4 is a fragmentary section view illustrating another embodiment of the invention;

FIG. 5 is a fragmentary section view illustrating a retractable syringe needle insert which can be attached to and used with conventional syringe bodies.

DETAILED DESCRIPTION OF THE INVENTION

Figure 1:
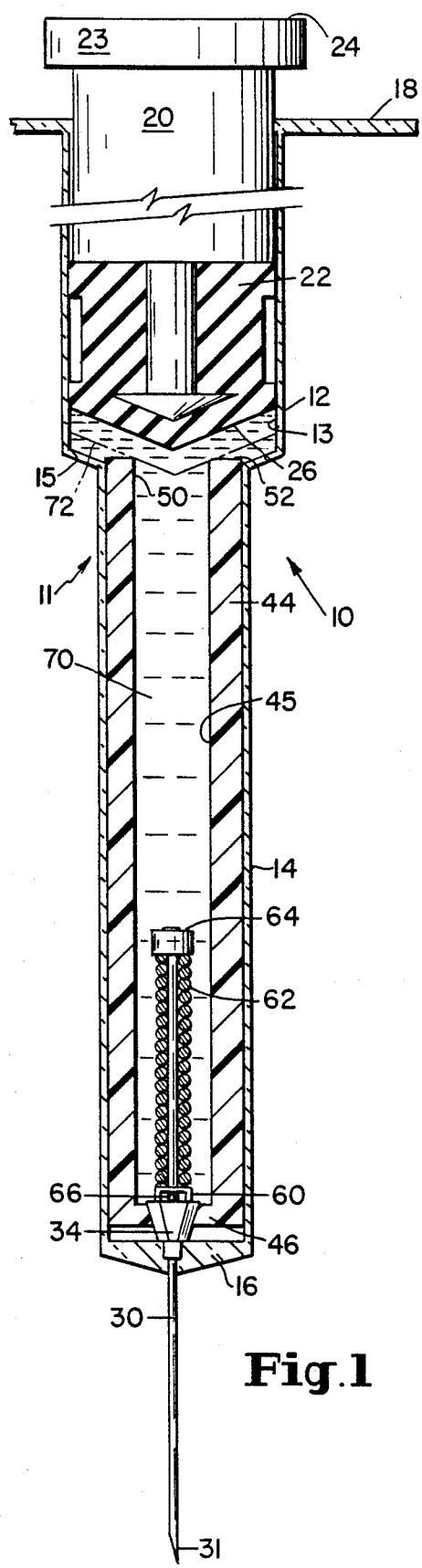
FIG. 1 is a fragmentary sectional view of one embodiment of the novel retractable needle syringe of the invention illustrating the needle retained in its extended operative injection position.
Figure 2:
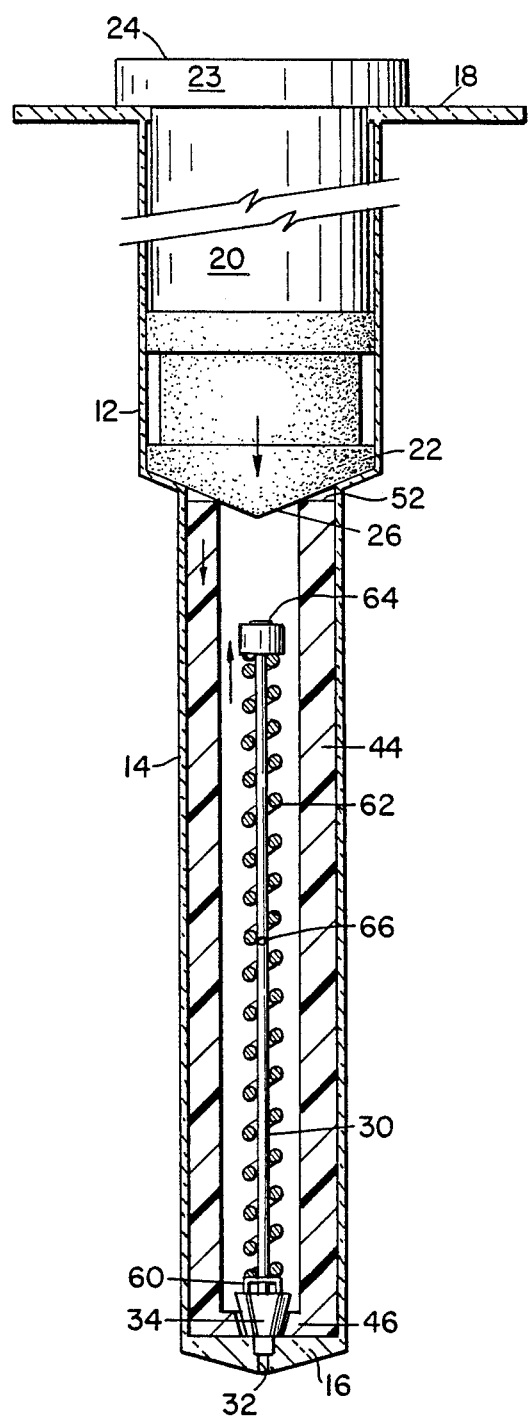
FIG. 2 is a view similar to FIG. 1, but illustrating the needle in its retracted position following use.

Referring to FIGS. 1-3, the novel syringe 10 of the invention, shown about five times actual size, includes a clear plastic cylindrical barrel 11 comprising a rear tubular section 12 having a bore 13, a forward tubular section 14 connected to section 12 via a tapered transition area 15, and a front wall 16 closing section 14. The rear end of section 12 is open and has an annular flange 18 formed therearound to be grasped by a person's fingers. A plastic plunger 20 has an annular, resilient rubber piston 22 mounted on its inner end for reciprocable sealing engagement within bore 13. The outer end of plunger 20 extends out of the open end of section 12 and has an enlarged head 23 with an end face 24 engageable by the thumb. The inner end face 26 of piston 22 is cone-shaped in correspondence with area 15.

In FIG. 1 a hollow needle 30 having an outer sharp end 31 is shown extending beyond wall 16 ready for insertion into a patient. Needle 30 slidably passes through a bore 32 of an expansible split locking collet 34 which has a circular end portion 36 press fitted within end wall 16 and a split tapered cone portion 38 formed with a plurality of radial slits 40 and a tapered external surface 42.

A cylindrical clear plastic actuating release tube 44 having a bore 45 fits snug but slidable within the bore of section 14 and has an outer end wall or chuck 46 having a tapered opening 48 corresponding to tapered surface 42. The open end 50 of bore 45 is in open communication with bore 13 and terminates at an abutment end face 52. In the inner lock position of tube 44 shown in FIGS. 1 and 3, chuck 46 and opening 48 engage against the large diameter area of surface 42 to squeeze and close collet section 38 around needle 30 and thereby lock the needle in its extended position. As shown, chuck 46 is spaced from end wall 16.

Needle 30 extends inwardly within tube 44 through an open fluid flow cage 60 resting on collet 34 and a fully compressed spring 62 which acts between cage 60 and a collar 64 fixed on the end of needle 30. The needle has a fluid opening 66 through its side wall in the area located within cage 60.

As shown in FIGS. 1 and 3 syringe 10 is ready for use, but plunger 20 will be fully retracted and bores 13 and 45 will be filled with fluid 70 to be injected into a patient. A medical person grasps the syringe with one hand, applying two fingers behind flange 18 and a thumb against face 24 of plunger 20. After needle end 31 is inserted into the patient, plunger 20 is slowly and evenly depressed forwardly, forcing fluid 70 forwardly through bores 13 and 45 into opening 66 and needle 30. Toward the end of its stroke plunger 20 reaches at a position 72, shown in phantom, where surface 26 engages against face 52 of tube 44, but is spaced a short distance from section 15. Head 23 is also spaced from flange 18. Thus, as needle 30 is removed from the skin of the patient, an extra forward axial push is given to plunger 20 to push tube 44 axially forwardly to the position of FIG. 2, thereby freeing tapered opening 48 from surface 42, permitting collet 34 to expand and release needle 30. Spring 62 expands and retracts needle 30 forwardly wholly within bore 45. Once retracted, needle 30 is retained in bore 45 by the spring force of spring 62 and can not be accidentally extended again through opening 32.

It is apparent that at the end of the injection and as needle 30 is removed from the patient's skin the needle is immediately automatically retracted within bore 45 by the medical person, using the same inward forward thumb movement against face 24 as is used in administering the shot. The medical person need not release the syringe from his hand or use a different finger or thumb motion, or use his other hand to cause the needle to retract. Consequently, the danger of an accidental scratch or prick from an exposed used needle is eliminated.

Another embodiment of the invention is illustrated in FIG. 4 and operates in principle in the same manner as the embodiment of FIGS. 1 and 2. In FIG. 4, actuator tube 80 has an opening 82 at its inner end and an expansible collet section 84 at its outer end engaging against the tapered wall section 86 of barrel section 88. A two-piece piston and seal assembly 90 includes a collar 91 fixed on needle 92 and a resilient seal 94 slidably surrounding collar 91. Compressed spring 96 acts between collar 91 and end wall 89. Needle 92 has a fluid opening 98 above collar 91, the needle extending inwardly and terminating in a barb 100 formed on its inner end. Thus, as in FIG. 1, when piston 102 of plunger 104 pushes actuator tube 80 forwardly to expand collet 84 and release assembly 90, needle 92 is automatically retracted within barrel section 88 as spring 96 expands. Barb 100 punctures the resilient membrane of piston 102 and this then holds the needle in its retracted position, together with the force of spring 96.

A secondary locking and release mechanism for needle 92 may take the form of an adhesive coating 110 (FIG. 4) bonding piston 91 to seal 94, the coating being inert, dimensionally stable, and soluble in the fluid injected. Thus, after the fluid has been injected if for some reason collet 84 fails to expand and release assembly 90, coating 110 will eventually dissolve from contact with the fluid. Piston 91 is then free to slide within seal 94 and needle 92 will automatically retract as spring 96 expands.

The invention may also be embodied in an insert unit 110 (shown in FIG. 5) which is readily attachable to an existing conventional syringe body 112 having a depressable plunger 114 therein, a discharge spout 116, and a threaded cavity 118 surrounding spout 116. Insert 110 includes a barrel 120 having a flange 122 at its open inner end which threads into cavity 118. Hollow needle 124 extends through expansible collet 126 which is squeezed around the needle by the end wall 128 of actuator tube 130 in the same manner as in the embodiment of FIGS. 1-3. The upper end of tube 130 has an open reduced neck portion 132 which fits within spout 116, the end face 134 of neck 132 extending far enough within body 112 to be engaged by plunger 114 toward the end of its stroke. Compressed spring 136 surrounds needle 124 and acts against a piston and seal assembly 138 fixed on the inner end 140 of needle 124. Inner end 140 of needle 124 is in open fluid communication with the bore of tube 130.

As in the embodiment of FIGS. 1-3, as plunger 114 pushes against end face 134 to move tube 130 axially forwardly within barrel 120, freeing end wall 128 from collet 126, needle 124 is automatically retracted within tube 130 as spring 136 expands. The availability of insert 110 enables a medical facility to enjoy the benefits and advantages of the invention, and still use up any conventional existing syringe bodies they may have in inventory.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A syringe for one-time use comprising tubular means including a rearward tubular section having a first open end and a forward tubular section extending forwardly from said rearward section and including a second closed end, needle means slidably mounted through said closed end for movement from a first position in which it extends beyond said closed end and a second position in which it is retracted within said tubular means, locking means for locking said needle means in said first position, bias means for urging said needle means from said first position to said second position, plunger means mounted in said rearward tubular section and forwardly displaceable toward said second end to dispense fluid contained in said tubular means through said needle means into a patient, release means responsive to forward movement of said plunger means to automatically release said locking means and cause said bias means to move said needle means to said second position, said release means including tubular actuator means separate from said plunger means and movably mounted within said forward tubular section from a rearward position to a forward position in which it releases said locking means, said tubular actuator means having rear abutment means engagable by said plunger means toward the end of its stroke and moved by said plunger means from said rearward position to said forward postion as forward displacement of said plunger means is continued for a short distance.

2. The syringe according to claim 1, said locking means including expansible collet means having a closed condition in which it holds said needle means in its first extended position and an expanded condition in which it releases said needle means, said tubular actuator means including chuck means associated with said collet means to release said collet means upon forward movement of said tubular actuator means by said plunger means.

3. The syringe according to claim 1, said locking and release means comprising an adhesive coating material which deteriorates after contact with the fluid being dispensed, thereby releasing said needle means for movement to its second retracted position.

4. The syringe according to claim 1, said needle means including barb means for grasping onto said plunger when said needle means is in said second retracted position.

5. The syringe of claim 1, said tubular actuator means fitting snug within said forward tubular section.

6. The syringe of claim 5, said tubular actuator means receiving said needle means when said needle means is in its retracted second position.

7. A needle assembly for attachment to a syringe body containing a fluid and having a plunger therein displaceable in a forward direction to dispense the fluid from an open forward end thereof, said needle assembly comprising tubular means having a first open end adapted to be connected to the forward end of said body and a second closed end, needle means slidably mounted through said closed end for movement from a first position in which it extends beyond said closed end and a second position in which it is retracted within said tubular means, locking means for locking said needle means in said first position, bias means for urging said needle means from said first position to said second position, release means including tubular actuator means separate from said plunger and movably mounted within said tubular means from a rearward position to a forward position in which it releases said locking means, said actuator means having rear abutment means adapted to extend into the syringe body and be engaged by said plunger toward the end of its stroke and moved by said plunger from said rearward position to said forward position as forward displacement of said plunger is continued for a short distance.

8. The needle assembly according to claim 7, said locking means including expansible collet means having a closed condition in which it holds said needle means in its first extended position and an expanded condition in which it releases said needle means, said tubular actuator means including chuck means associated with said collet means to release said collet means upon forward movement of said tubular actuator means by said plunger means.

9. The needle assembly at claim 7, said tubular actuator means fitting snug within said tubular means.

10. The syringe of claim 9, said tubular actuator means receiving said needle means when said needle means is in its retracted second position.

11. A syringe for one-time use comprising tubular means including a rearward tubular section having a first open end and a forward tubular section extending forwardly from said rearward section and including a second closed end, needle means slidably mounted through said closed end for movement from a first position in which it extends beyond said closed end and a second position in which it is retracted within said tubular means, locking means for locking said needle means in said first position, bias means for urging said needle means from said first position to said second position, plunger means mounted in said rearward tubular section and forwardly displaceable toward said second end to dispense fluid contained in said tubular means through said needle means into a patient, release means responsive to forward movement of said plunger means to automatically releases said locking means and cause said bias means to move said needle means to said second position, said release means including tubular actuator means movably mounted within said forward tubular section from a rearward position to a forward position in which it releases said locking means, said tubular actuator means having rear abutment means engagable by said plunger means toward the end of its stroke and moved by said plunger means from said rearward position to said forward position as forward displacement of said plunger means is continued for a short distance, said locking means including expansible collet means having a closed condition in which it holds said needle means in its first extended position and an expanded condition in which it releases said needle means, said tubular actuator means including chuck means associated with said collet means to release said collet means upon forward movement of said tubular actuator means by said plunger means.

12. A needle assembly for attachment to a syringe body containing a fluid and having a plunger therein displaceable in a forward direction to dispense the fluid from an open forward end thereof, said needle assembly comprising tubular means having a first open end adapted to be connected to the forward end of said body and a second closed end, needle means slidably mounted through said closed end for movement from a first position in which it extends beyond said closed end and a second position in which it is retracted within said tubular means, locking means for locking said needle means in said first position, bias means for urging said needle means from said first position to said second position, release means including tubular actuator means movably mounted within said tubular means from a rearward position to a forward position in which it releases said locking means, said tubular actuator means having rear abutment means adapted to extend into the syringe body and be engaged and moved by said plunger from said rearward position to said forward position as said plunger moves in its forward direction, said locking means including expansible collet means having a closed condition in which it holds said needle means in its first extended position and an expanded condition in which it releases said needle means, said tubular actuator means including chuck means associated with said collet means to release said collet means upon forward movement of said tubular actuator means by said plunger.

* * * * *